United States Patent

Motoyuki et al.

[11] Patent Number: 5,723,711
[45] Date of Patent: Mar. 3, 1998

[54] PROCESS FOR PREPARING 2-METHYLNAPHTHALENE

[75] Inventors: Masahiro Motoyuki; Koji Yamamoto, both of Kobe, Japan; John Paul McWilliams; Ajit Vishwanath Sapre, both of Paulsboro, N.J.

[73] Assignees: Kobe Steel, Ltd., Kobe, Japan; Mobil Oil Corporation, Fairfax, Va.

[21] Appl. No.: 744,828

[22] Filed: Nov. 6, 1996

[51] Int. Cl.⁶ .................................. C07C 5/22
[52] U.S. Cl. .......................... 585/481; 585/480
[58] Field of Search .................... 585/480, 481

[56] References Cited

U.S. PATENT DOCUMENTS 3,116,341  12/1963  Sheppard et al. .......... 585/480
4,982,040  1/1991   Angevine et al. .......... 585/475
5,243,113  9/1993   Nobusawa et al. .......... 585/315

OTHER PUBLICATIONS

Vorozhtsov et al. Zhurnal Obshchey khimii, 1959, vol. 29, nr 5, pp. 1541–1545 (USSR).

*Primary Examiner*—Glenn Caldarola
*Assistant Examiner*—Thuan D. Dang
*Attorney, Agent, or Firm*—Oblon, Spivak, McClelland, Maier & Neustadt, P.C.

[57] ABSTRACT

A process for producing 2-methylnaphthalene from a feedstock containing 1-methylnaphthalene by contacting the feedstock with a catalyst composition, in which the process comprising isomerization of 1-methylnaphthalene, wherein the catalyst composition comprising a synthetic zeolite characterized by an X-ray diffraction pattern including interplanar d-spacing as set forth in Table A of the specification.

13 Claims, No Drawings

PROCESS FOR PREPARING 2-METHYLNAPHTHALENE

FIELD OF THE INVENTION

This invention relates to a process for preparing 2-methylnaphthalene (2-MN) from 1-methylnaphthalene(1-MN) by using catalysts for isomerization of 1-MN.

BACKGROUND OF THE INVENTION

The compound 2-MN as well as 1-MN are contained in coaltar which is produced by coking of coal or in LCO(light cycle oil) which is obtained from the oil refining process. Concerning 2-MN, it is quite useful raw material, for example, 2-MN is used as a starting material in manufacturing Vitamin K of pharamaceuticals, or a precursor of 2,6-dimethylnaphthalene in the manufacture of heat resisting polyester resins.

By contrast, the effective use of 1-MN has not been developed in the industry, therefore the following methods to isomerize 1-MN to 2-MN have been proposed. V. Solinas et al. reported a process for isomerization of 1-MN in the presence of Y-zeolite as a catalyst [Applied Catalysis, 9(1984), p109–117]. Z. Popova et al. disclosed isomerization of 1-MN to 2-MN by using a zeolite H-ZSM5 [React. Kinet. Catal. Lett., Vol.52, No. 1, p51–58 (1994)].

However, a catalitic life of each process was so short that the catalytic activity is reduced quickly by coking in the reaction.

Japanese Laid-open Hei5-201890 shows a process to isomerize 1-MN by employing a zeolite on which metals such as Ni or Pd etc. are carried, over feeding Hydrogen gas in a reactor. According to this process, the catalytic life can be extended, however, the preparing process of the catalyst is complicated and is not desirable economically, and it also produces unfavorable byproduct (other alkylnaphthalenes except 1-MN and 2-MN) such as dimethylnaphthalene, ethylnaphthalene and so on.

SUMMARY OF THE INVENTION

The present invention has been made in view of the foregoing situation and it intends to provide a process for preparing 2-methylnaphthalene, in which an employed catalyst exhibits high selectivity of 2-MN and low conversion rate to undesirable byproduct as well as long catalytic activity.

Provided herein is a process for producing 2-MN from a feedstock containing 1-MN by contacting said feedstock with a catalyst composition, said process comprising isomerization of 1-MN, wherein said catalyst composition comprising a synthetic zeolite characterized by an X-ray diffraction pattern including interplanar d-spacing as set forth in Table A.

TABLE A

| interplanar d-spacing (Å) | relative intensity $I/I_o \times 100$ |
| --- | --- |
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | W–S |

TABLE A-continued

| interplanar d-spacing (Å) | relative intensity $I/I_o \times 100$ |
| --- | --- |
| 3.91 ± 0.07 | M–VS |
| 3.42 ± 0.06 | VS |

*The relative intensities are given in terms of the symbols: W = weak, M = medium, S = strong, VS = very strong.

DESCRIPTION OF THE PREFERRED EMBODIMENTS

The present inventors have made earnest studies to utilize 1-MN effectively, as a result, have accomplished the present invention by employing a particular catalyst in the isomerization of 1-MN.

The particular catalyst is a zeolite which comprises a synthetic porous crystalline material characterized by an X-ray diffraction pattern including interplanar d-spacing can be set forth in the Table A.

The zeolite is known as MCM-22 and the entire contents of application Ser. No. 5,001,295 are incorporated herein by reference.

Isomerization conditions include a temperature of between 300° to 400° C., and preferably between 350° and 400° C., and a pressure of between 0 to 100 kg/cm$^2$.G and preferably 5 to 50 kg/cm$^2$.G.

The reaction is accomplished utilizing a feed weight hourly space velocity (WHSV) of between 0.1 to 500 hr$^{-1}$, and suitably 0.5 to 10 hr$^{-1}$. In case WHSV is too high, contacting time between a feedstock and the catalyst is not enough and the conversion rate of 1-MN is low. On the contrary, when WHSV is too low, it means the reactor requires to be large in the volume to accommodate much more catalyst, or the supply of the feedstock should be decreased in amount, therefore productivity in the isomerization is reduced.

In the isomerization of the present invention, the content of 1-MN in a feedstock is desirable to be more than 35 weight %, more preferably the content of 1-MN is more than 50 weight %. The feedstock can be supplied into a reactor in the liquid or gaseous phase, and gaseous phase is preferable.

Furthermore, the present invention provides a process for producing 2-MN from a feedstock containing 1-MN by contacting the feedstock with the catalyst MCM-22, comprising a step for isomerization of 1-MN to produce 2-MN, and a step for separation of 2-MN from the product in the isomerization.

As a method for separation of 2-MN, any method which is known for separation of isomers, such as distillation, crystallization, adsorption or extraction, can be used. However, to obtain high yield of 2-MN from the mixture of MN isomers, distillation and crystallization are preferable.

In this process, it is recommendable to recycle 1-MN fraction which is separated from the product as a feedstock for isomerization.

The present invention will now be explained refering to examples.

EXAMPLE 1

153 grams of MCM-22 (¼"D×⅛"L, cylindrical pellet) were charged in a tubular reactor (volume: 350 cc). The reactor was heated from room temperature to 270° C. at the rate of 100° C./hr. The pressure in the reactor was controlled to 5 kg/cm².G by introducing hydrogen gas into the reactor by the rate of 1.0 scf/hr at atmospheric pressure. Then the introducing rate of hydrogen gas was increased up to 2.55 scf/hr, and a feedstock (1-MN:96.5%, 2-MN:1.1%, others:2.4%) was introduced into the reactor at the rate of 153 g/hr(Total WHSV was 1 hr⁻¹).

The temperature in the reactor was raised to 350° C. in 10 hours after the feedstock was introduced into the reactor. The experiment was carried out for ten days after the temperature in the reactor became 350° C., and the content of the obtained product was analyzed by gas chromatography everyday. The result of each day is shown in Table B ["1-1" means the result after 1st day, and "1-10" means the result after ten days].

TABLE B

| | Feed-stock | Example 1 | | | | |
|---|---|---|---|---|---|---|
| | | 1-1 | 1-2 | 1-3 | 1-4 | 1-5 |
| 1-MN (wt %) | 96.50 | 29.14 | 29.93 | 29.18 | 29.19 | 29.53 |
| 2-MN (wt %) | 1.10 | 67.40 | 67.12 | 67.45 | 67.04 | 67.86 |
| dimethylnaphthalenes (wt %) | 0 | 0.48 | 0.93 | 0.28 | 0.19 | 0.08 |
| ethylnaphthalenes (wt %) | 0.28 | 0.28 | 0.28 | 0.28 | 0.28 | 0.29 |
| naphthalene (wt %) | 0 | 0.57 | 0.47 | 0.36 | 0.32 | 0.28 |
| Others (wt %) | 2.12 | 2.13 | 2.22 | 2.44 | 2.98 | 1.97 |
| Total MNs (wt %) | 97.60 | 96.54 | 96.10 | 96.63 | 96.23 | 97.39 |
| 2-MN/1-MN | 0.01 | 2.31 | 2.32 | 2.31 | 2.30 | 2.30 |
| 2-MN Selectivity (%) | — | 95.12 | 94.51 | 95.24 | 94.67 | 96.29 |
| 1-MN Conversion (%) | — | 69.81 | 69.97 | 69.76 | 69.75 | 69.40 |
| Others except MNs (wt %) | 2.40 | 3.46 | 3.90 | 3.37 | 3.77 | 2.61 |

| | 1-6 | 1-7 | 1-8 | 1-9 | 1-10 |
|---|---|---|---|---|---|
| 1-MN (wt %) | 96.50 | 39.58 | 29.87 | 30.15 | 30.40 | 30.64 |
| 2-MN (wt %) | 1.10 | 67.44 | 67.44 | 67.22 | 66.88 | 65.48 |
| dimethylnaphthalenes (wt %) | 0 | 0.14 | 0.06 | 0.06 | 0.06 | 0.05 |
| ethylnaphthalenes (wt %) | 0.28 | 0.29 | 0.28 | 0.29 | 0.29 | 0.29 |
| naphthalene (wt %) | 0 | 0.38 | 0.27 | 0.22 | 0.21 | 0.20 |
| Others (wt %) | 2.12 | 2.17 | 2.26 | 2.08 | 2.17 | 3.35 |
| Total MNs (wt %) | 97.60 | 97.02 | 97.31 | 97.36 | 97.28 | 96.12 |
| 2-MN/1-MN | 0.01 | 2.28 | 2.26 | 2.23 | 2.20 | 2.14 |
| 2-MN Selectivity (%) | — | 95.77 | 95.93 | 96.22 | 96.10 | 94.41 |
| 1-MN Conversion (%) | — | 69.34 | 69.05 | 68.76 | 68.49 | 68.24 |
| Others except MNs (wt %) | 2.40 | 2.98 | 2.69 | 2.64 | 2.72 | 3.88 |

(Note)
"2-MN selectivity" means a ratio of "2-MN/(product − 1-MN)".

EXAMPLE 2–5

(EXAMPLE 2)

After the experiment of Example 1, the introducing rate of hydrogen gas was increased up to 3.85 scf/hr, and the feed rate of the feedstock was increased to 230 g/hr (Total WHSV was 1.5 hr⁻¹). The experiment was carried out for one day, and the content was analyzed by gas chromatography.

(EXAMPLE 3)

After the experiment of Example 2, the introducing rate of hydrogen gas was increased up to 5.15 scf/hr, and the feed rate of the feedstock was increased to 306 g/hr (Total WHSV was 2 hr⁻¹). At the same time, the temperature in the reactor was changed to 375° C. The experiment was carried out for one day, and the content was analyzed by gas chromatography.

(EXAMPLE 4)

After the experiment of Example 3, the temperature in the reactor was changed to 400° C. The experiment was carried out for one day, and the content was analyzed by gas chromatography.

The results of each Example are shown in Table C.

TABLE C

| | Feed-stock | Example No. | | |
|---|---|---|---|---|
| | | 2 | 3 | 4 |
| Temperature (°C.) | — | 350 | 375 | 400 |
| Pressure (kg/cm² · G) | — | 5 | 5 | 5 |
| WHSV (hr⁻¹) | — | 1.5 | 2 | 2 |
| Hydrogen feed (cft/h) | — | 3.85 | 5.15 | 5.15 |
| 1-MN (wt %) | 96.50 | 35.41 | 37.48 | 33.76 |
| 2-MN (wt %) | 1.10 | 61.97 | 59.82 | 63.48 |
| dimethylnaphthalenes (wt %) | 0 | 0 | 0 | 0 |
| ethylnaphthalenes (wt %) | 0.28 | 0.29 | 0.30 | 0.28 |
| naphthalene (wt %) | 0 | 0.14 | 0.13 | 0.22 |
| Others (wt %) | 2.12 | 2.19 | 2.27 | 2.27 |
| Total MNs (wt %) | 97.0 | 97.38 | 97.30 | 97.23 |
| 2-MN/1-MN | 0.01 | 1.75 | 1.60 | 1.88 |
| 2-MN Selectivity (%) | — | 95.94 | 95.68 | 95.82 |
| 1-MN Conversion (%) | — | 63.31 | 61.16 | 65.02 |
| Others except MNs (wt %) | 2.40 | 2.62 | 2.70 | 2.77 |

As can be seen from Table B and C, according to the present invention, high yield of 2-MN can be obtained for a long period, and the conversion rate to the byproduct is quite low (less than 4%).

What is claimed is:

1. A process for producing 2-methylnaphthalene from a feedstock containing 1-methylnaphthalene by contacting said feedstock with a catalyst composition, said process comprising isomerization of 1-methylnaphthalene,
   wherein said catalyst composition comprises a synthetic zeolite characterized by an X-ray diffraction pattern including interplanar d-spacing as set forth in Table A of the specification.

2. The process for producing 2-methylnaphthalene as defined in claim 1, wherein said isomerization is carried out under conditions including
   a temperature of between 300° to 400° C.,
   a pressure of between 0 to 100 kg/cm².G
   and a feed weight hourly space velocity of between 0.1 to 500 hr⁻¹.

3. The process for producing 2-methylnaphthalene from a feedstock containing 1-methylnaphthalene of claim 1 comprising the following steps:
   I. isomerization of 1-methylnaphthalene to 2-methylnaphthalene, and
   II. separation of 2-methylnaphthalene from the product in said step I.

4. The process for producing 2-methylnaphthalene as defined in claim 3, wherein 1-methylnaphthalene in step II is recycled to step I as the feedstock.

5. The process of claim 1, wherein isomerization is conducted at a temperature of from 300° to 400° C.

6. The process of claim 1, wherein isomerization is conducted at a temperature of from 350° to 400° C.

7. The process of claim 1, wherein isomerization is conducted at a pressure of between 0 and 100 gm/cm².G.

8. The process of claim 1, wherein isomerization is conducted at a pressure of between 5 and 50 kg/cm².G.

9. The process of claim 1, wherein isomerization is conducted at a feed weight hourly space velocity of from 0.1 to 500 hr⁻¹.

10. The process of claim 1, wherein isomerization is conducted at a feed weight hourly space velocity of from 0.5 to 10 hr⁻¹.

11. The process of claim 1, wherein the content of 1-methylnaphthalene in said feedstock is more than 35 weight %.

12. The process of claim 1, wherein the content of 1-methylnaphthalene in said feedstock is more than 50 weight %.

13. The process of claim 1, wherein said synthetic zeolite is MCM-22.

* * * * *